US012651664B2

(12) United States Patent
Chen et al.

(10) Patent No.: US 12,651,664 B2
(45) Date of Patent: Jun. 9, 2026

(54) NODE STRUCTURE ENGINE

(71) Applicant: Chen Tech, LLC, Miami Gardens, FL (US)

(72) Inventors: Christopher James Chen, Fort Lauderdale, FL (US); Hernando Celada, Southwest Ranches, FL (US)

(73) Assignee: Chen Tech, LLC, Miami Gardens, FL (US)

( * ) Notice: Subject to any disclaimer, the term of this patent is extended or adjusted under 35 U.S.C. 154(b) by 578 days.

(21) Appl. No.: 18/307,125

(22) Filed: Apr. 26, 2023

(65) Prior Publication Data

US 2024/0274278 A1     Aug. 15, 2024

Related U.S. Application Data

(60) Provisional application No. 63/445,144, filed on Feb. 13, 2023.

(51) Int. Cl.
*G16H 40/20*          (2018.01)
*G06Q 10/0631*     (2023.01)
*G16H 50/30*         (2018.01)

(52) U.S. Cl.
CPC ..... *G16H 40/20* (2018.01); *G06Q 10/063114* (2013.01); *G16H 50/30* (2018.01)

(58) Field of Classification Search
CPC ................... G16H 40/20; G16H 50/30; G06Q 10/063114; G06N 5/01
See application file for complete search history.

(56) References Cited

U.S. PATENT DOCUMENTS 9,684,874 B2 *   6/2017   Cichosz ................. G06N 20/00
2015/0100344 A1 *   4/2015   Chen ...................... G16H 50/30
                                                                              705/2
2015/0339442 A1    11/2015   Oleynik

FOREIGN PATENT DOCUMENTS

CN          105792741 A  *  7/2016   ........... A61B 5/1118

OTHER PUBLICATIONS

CN105792741A Translation (Year: 2016).*
(Continued)

*Primary Examiner* — Schyler S Sanks
(74) *Attorney, Agent, or Firm* — Fish & Richardson P.C.

(57)          ABSTRACT

Methods, systems, and apparatus, including computer programs encoded on computer storage media, for updating a node structure. One of the methods includes: maintaining, in memory and for each indicator of a first entity, a corresponding tree structure identifying the corresponding indicator and attributes affecting the indicator, the tree structure having i) parent nodes representing indicators that are not actionable for the first entity and ii) leaf nodes representing an action for the first entity to adjust the indicator; determining whether a first tree structure includes a link with a second tree structure; determining a weight for a link between the first and second tree structures; and creating the link between the first and second tree structures that includes the weight; and maintaining the first and second tree structures and the link for generating a recommendation of an action to adjust a value of the first indicator for an entity.

20 Claims, 5 Drawing Sheets

(56)          References Cited

OTHER PUBLICATIONS

Wikipedia.com [online], "Decision tree learning," last edited on Mar. 16, 2022, retrieved from URL<http://en.wikipedia.org/w/index. php?title=Decision_tree_learning&oldid=1077440822>, 11 pages.
Wikipedia.com [online], "Decision tree," last edited on Mar. 28, 2022, retrieved from URL<http://en.wikipedia.org/w/index.php? title=Decision_tree&oldid=1079851424>, 11 pages.
Wikipedia.com [online], "Knowledge graph," last edited on Apr. 13, 2022, retrieved from URL<http://en.wikipedia.org/w/index.php? title=Knowledge_graph&oldid=10825065 45>, 5 pages.

* cited by examiner

Figure 2A:
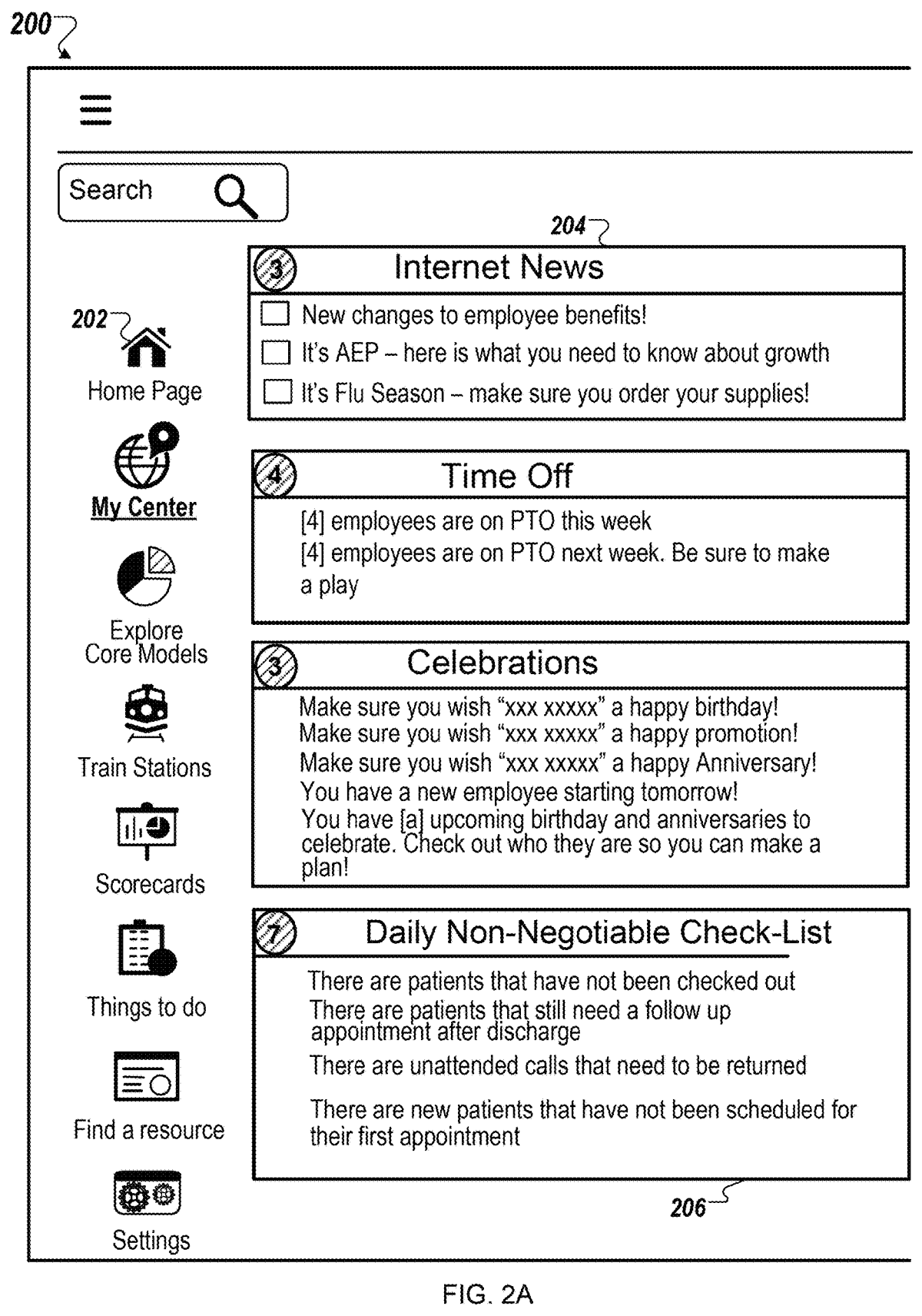

200

Search 🔍

202
🏠
Home Page

🌐
My Center

📊
Explore
Core Models

🚂
Train Stations

📊
Scorecards

📋
Things to do

🪪
Find a resource

⚙️
Settings

204
Internet News ③
☐ New changes to employee benefits!
☐ It's AEP – here is what you need to know about growth
☐ It's Flu Season – make sure you order your supplies!

Time Off ④
[4] employees are on PTO this week
[4] employees are on PTO next week. Be sure to make a play

Celebrations ③
Make sure you wish "xxx xxxxx" a happy birthday!
Make sure you wish "xxx xxxxx" a happy promotion!
Make sure you wish "xxx xxxxx" a happy Anniversary!
You have a new employee starting tomorrow!
You have [a] upcoming birthday and anniversaries to celebrate. Check out who they are so you can make a plan!

Daily Non-Negotiable Check-List ⑦
There are patients that have not been checked out
There are patients that still need a follow up appointment after discharge
There are unattended calls that need to be returned
There are new patients that have not been scheduled for their first appointment

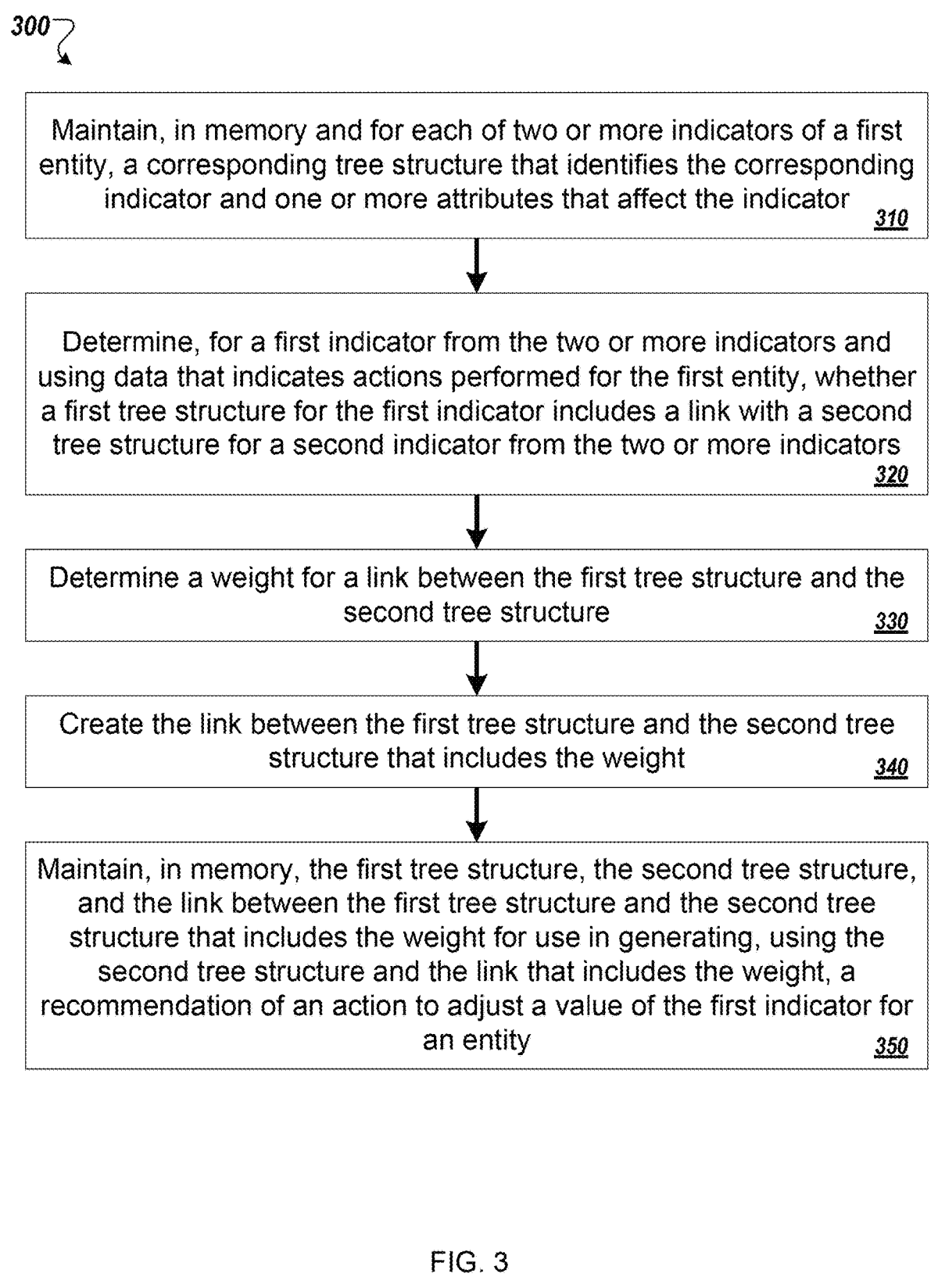

Maintain, in memory and for each of two or more indicators of a first entity, a corresponding tree structure that identifies the corresponding indicator and one or more attributes that affect the indicator     *310*

Determine, for a first indicator from the two or more indicators and using data that indicates actions performed for the first entity, whether a first tree structure for the first indicator includes a link with a second tree structure for a second indicator from the two or more indicators     *320*

Determine a weight for a link between the first tree structure and the second tree structure     *330*

Create the link between the first tree structure and the second tree structure that includes the weight     *340*

Maintain, in memory, the first tree structure, the second tree structure, and the link between the first tree structure and the second tree structure that includes the weight for use in generating, using the second tree structure and the link that includes the weight, a recommendation of an action to adjust a value of the first indicator for an entity     *350*

FIG. 3

NODE STRUCTURE ENGINE

CROSS-REFERENCE TO RELATED PATENT APPLICATIONS

This application claims the benefit of U.S. Provisional Application No. 63/445,144 filed on Feb. 13, 2023, the contents of which are incorporated by reference herein.

BACKGROUND

Classification and regression tree (CART) analysis can build decision trees that can predict an outcome in response to whether or not certain conditions are met. The organization of a decision tree can reflect relationships between variables in data sets. Knowledge graphs are another way to visualize and find previously unknown connections between variables in data sets.

SUMMARY

Artificial intelligence (AI) architectures can include interconnected node structures, e.g., knowledge graphs or decision trees. Generally, to train a model, training data passes through layers of nodes. During training, the connections between the nodes are altered, e.g., changing weights in mathematical transformations, so that the trained model yields the desired results. Nodes that are not linked generally cannot communicate with one another. In some implementations, more dynamic architectures can allow communicating between unconnected nodes by creating new links.

In some action recommendation systems, parent nodes can correspond to indicators, e.g., associated with input values, and leaf nodes can indicate action recommendations. If, for example, input data contains multiple indicators of an entity, e.g., a person, and the parent nodes corresponding to the indicators are not connected in the node structure, a trained model cannot determine that there might be a correlation between those two parent nodes, and the quality of the action recommendation generated by the trained model can suffer. To address this, a system can create new links between parent nodes in a node structure when the nodes did not already have links, which can result in more powerful and complex recommendation systems.

In some implementations, connecting parent nodes can result in arriving at action recommendations that represent actions that can be taken by the system to enhance the security of the architecture. For example, the action could lead to a reduced risk of a computer network attack for the entity. The recommendation can be a better recommendation than a system would otherwise generate without the creation of the new links.

The AI capabilities discussed can be directly connected to a user interface (UI). This direct connection can reduce the time passed before a user takes action. For instance, the UI can present the indicators and action recommendations in a clear and organized manner that increases readability, reduces eyestrain, or both, for the user. The UI can enable a user to see multiple action recommendations, including ones that conflict, or don't otherwise align, which can occur in complex situations, e.g., medical cases. In medical cases, presenting action recommendations directly in the UI and designing the recommendation and training engines in a way to create complex action recommendation can potentially expose gaps in health care.

In general, one aspect of the subject matter described in this specification can be embodied in methods that include the actions of: maintaining, in memory and for each of two or more indicators of a first entity, a corresponding tree structure that identifies the corresponding indicator and one or more attributes that affect the indicator, the tree structure having i) one or more parent nodes each of which represent indicators that are not actionable for the first entity and ii) one or more leaf nodes each of which represent an action that can be performed for the first entity to adjust a value of the indicator; determining, for a first indicator from the two or more indicators and using data that indicates actions performed for the first entity, whether a first tree structure for the first indicator includes a link with a second tree structure for a second indicator from the two or more indicators; in response to determining that the first tree structure does not include the link with the second tree structure: determining a weight for a link between the first tree structure and the second tree structure; and creating the link between the first tree structure and the second tree structure that includes the weight; and maintaining, in memory, the first tree structure, the second tree structure, and the link between the first tree structure and the second tree structure that includes the weight for use in generating, using the second tree structure and the link that includes the weight, a recommendation of an action to adjust a value of the first indicator for an entity.

Other embodiments of this aspect include corresponding computer systems, apparatus, computer program products, and computer programs recorded on one or more computer storage devices, each configured to perform the actions of the methods. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The foregoing and other embodiments can each optionally include one or more of the following features, alone or in combination.

In some implementations, determining the weight includes determining the weight that indicates an amount by which one or more nodes in the second tree structure affect the value of the first indicator.

In some implementations, creating the link includes creating a unidirectional link between the first tree structure and the second tree structure.

In some implementations, creating the link includes creating a bi-directional link between the first tree structure and the second tree structure.

In some implementations, the actions include determining a second weight that indicates an amount by which one or more nodes in the first tree structure affect the second indicator. The weight can indicate an amount by which one or more nodes in the second tree structure affect the first indicator; and creating the link can include creating the link that includes the weight and the second weight.

In some implementations, creating the link includes creating a link between a first root node of the first tree structure and a second root node of the second tree structure.

In some implementations, creating the link includes creating a link between a first non-root node of the first tree structure and a second non-root node of the second tree structure.

In some implementations, creating the link includes creating a link between a first root node of the first tree structure and a second non-root node of the second tree structure.

In some implementations, the actions includes: maintaining, for each of the two or more indicators for the first entity, a first set of weights for nodes in the corresponding tree structure; maintaining, for each of the two or more indicators for a second different entity, a second different set of weights for nodes in the corresponding tree structure; determining, for the first entity and using the first set of weights, a first recommendation of a first action to adjust a value of the first indicator for the first entity; and determining, for the second different entity and using the second different set of weights, a second recommendation of a second different action to adjust a value of the first indicator for the second different entity.

In some implementations, the action includes an automated action performed automatically by a system.

In some implementations, each root node in the tree structures represents a key performance indicator.

In some implementations, the first entity includes a patient or a health care provider.

In some implementations, the one or more actions comprise actions performed to reduce a risk of readmission by the first entity to a hospital.

In some implementations, the actions include: receiving, from a device, a first subset of second data indicating input in a user interface of at least one of two or more second indicators of another entity; receiving, from a database different from the device, a second subset of the second data that represents at least one of the two or more second indicators of the other entity; determining, using the link between the first tree structure and the second tree structure and the two or more second indicators of the other entity, the recommendation of the action to reduce risk for the other entity; and providing, to the device, second data for the recommendation to cause the device to present, using the second data, the recommendation in the user interface.

In some implementations, receiving the data includes receiving, from the database different from the device, the second subset of the second data that represents the at least one of the two or more second indicators of the other entity.

In some implementations, providing the second data includes providing the second data for the recommendation to cause the device to present, in a unified user interface, the recommendation and at least two of the two or more second indicators of the other entity, the at least two of the two or more second indicators including a first indicator received from the device and a second indicator received from the database different from the device.

In some implementations, the actions include receiving first data that represents an initial recommendation for the first entity and second data that represents an indicator of the first entity. Determining whether the first tree structure can include a link with the second tree structure includes determining whether the tree structures for the two or more indicators include a link between the initial recommendation for the first entity and the indicator of the first entity. Creating the link can include, in response to determining that the tree structures for the two or more indicators do not include a link between the initial recommendation and the indicator, creating the link between the initial recommendation and the indicator. The initial recommendation and the indicator can each be in separate ones of the first tree structure and the second tree structure.

In some implementations, the second tree structure includes a first parent node that represents the initial recommendation and the first tree structure includes a second parent node that represents the indicator.

In some implementations, the actions can include receiving first data that represents a first recommendation for the first entity and second data that represents a second recommendation for the first entity. Determining whether the first tree structure includes a link with the second tree structure can include determining whether the tree structures for the two or more indicators include a link between the first recommendation for the first entity and the second recommendation for the first entity. Creating the link can include, in response to determining that the tree structures for the two or more indicators do not include the link between the first recommendation and the second recommendation, creating the link between the first recommendation in the first tree structure and the second recommendation in the second tree structure.

In some implementations, the actions can include: accessing, for another entity, the link between the first tree structure and the second tree structure using two or more second indicators for the other entity; and generating, using the link between the first tree structure and the second tree structure that represents one or more positive correlations between a) the two or more second indicators for the other entity and b) the first recommendation and the second recommendation, a recommendation of an action to reduce risk for the other entity.

This specification uses the term "configured to" in connection with systems, apparatus, and computer program components. That a system of one or more computers is configured to perform particular operations or actions means that the system has installed on it software, firmware, hardware, or a combination of them that in operation cause the system to perform those operations or actions. That one or more computer programs is configured to perform particular operations or actions means that the one or more programs include instructions that, when executed by data processing apparatus, cause the apparatus to perform those operations or actions. That special-purpose logic circuitry is configured to perform particular operations or actions means that the circuitry has electronic logic that performs those operations or actions.

The subject matter described in this specification can be implemented in various embodiments and may result in one or more of the following advantages. In some implementations, the training engine and corresponding methods described in this specification can create a node structure architecture that results in recommending actions that would not have otherwise been considered, e.g., to improve the health of a patient or increase computer network security. In some implementations, presentation of an action recommendation in a UI can enable fast and seamless communication of the action recommendation and indicators of health to a member of a care team, e.g., enables action value tracking. The design of the UI can result in an enhanced user experience, readability, comprehension and reduced eyestrain. In some implementations, a training engine can create a node structure that generates a single recommendation from multiple recommendations associated with multiple members of a care team, which can lead to more holistic and effective treatment of a patient.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIGS. 2A-B depict an example of unified user interface.

FIG. 3 is a flow diagram of an example process for using a node structure for action recommendations.

Like reference numbers and designations in the various drawings indicate like elements.

DETAILED DESCRIPTION

A recommendation engine can take several forms, including decision trees or knowledge graphs. The recommendation engine can traverse a node structure to arrive at action recommendations that are likely to improve computer network security or the health of a patient, reduce risk for the entity, or both. The strength of the correlation between nodes in a connection graph can guide the recommendation engine to an appropriate leaf node, representing an action recommendation.

A heuristic element to the AI node structure can enable a training engine to adjust weights in the decision tree or connection graph. When creating the node structure, the training engine can determine connections between nodes in the node structure that did not previously exist. The training engine can update the node structure with data indicating these connections, enabling the recommendation engine to make jumps when traversing the node structure that were not previously available. With the ability to jump throughout the node structure, the recommendation engine can make action recommendations in unprecedented ways, e.g., considering survey results from a patient in addition to medical records of that same patient or improving the security of the node structure.

Figure 1:
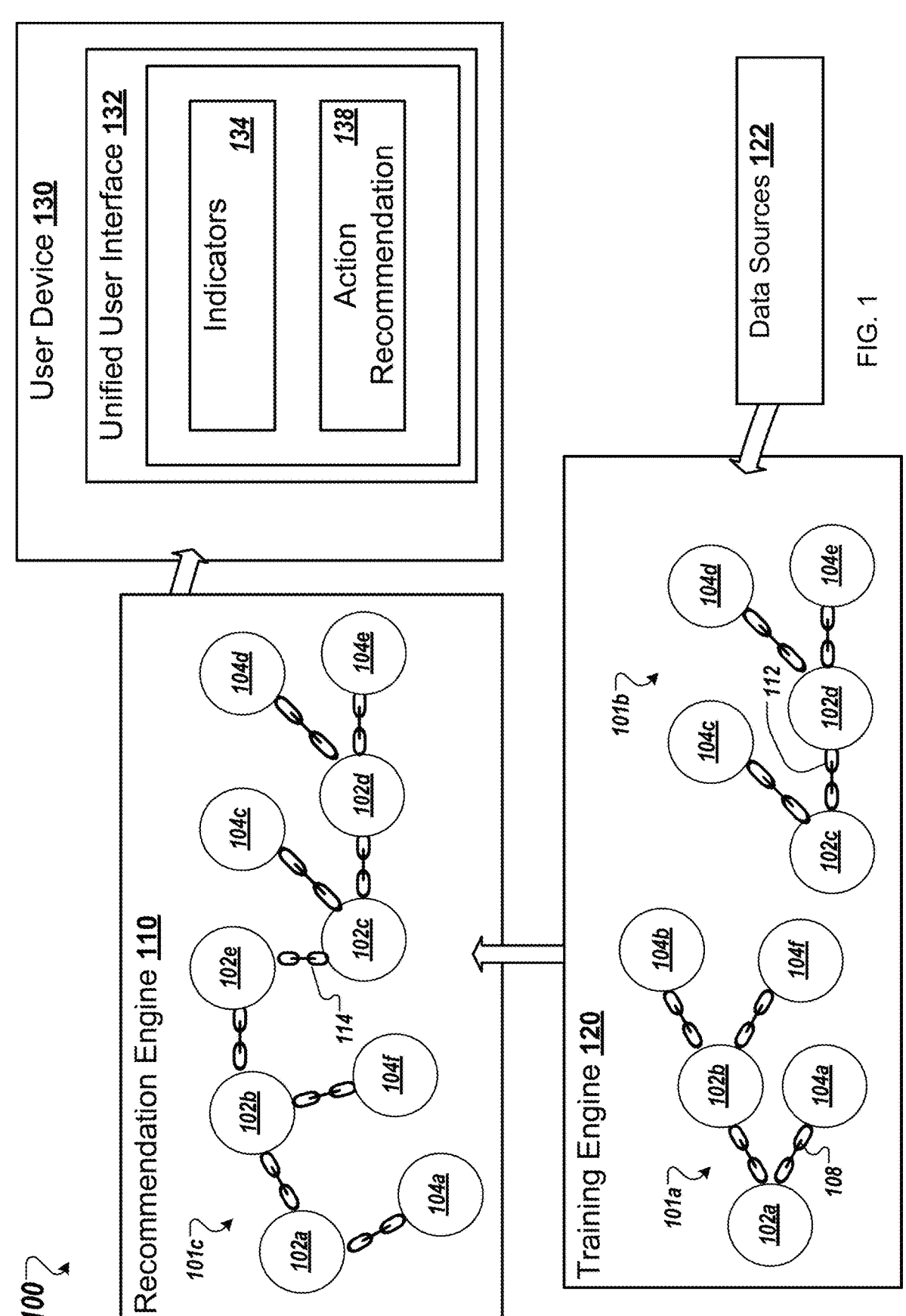
FIG. 1 depicts an example environment in which a node structure is trained and used to determine action recommendations.

FIG. 1 depicts an example environment 100 in which a node structure is trained and used to determine action recommendations. The environment 100 can include a recommendation engine 110, a training engine 120, a user device 130, and data sources 122. The data sources 122 can be any appropriate type of data sources, such as databases, servers, or a combination of these, that are external to the training engine 120, e.g., a system that includes the training engine 120 and the recommendation engine. The training engine 120 uses data from the data sources 122 to generate and update the node structure. The recommendation engine 110 can use the updated node structure to provide action recommendations to devices such as the user device 130.

Each individual data source of the one or more data sources 122 can contain one or more indicators that describe a computer network, various entities, or a combination of both. In some implementations, indicators can relate to computer network security, such as permissions data, data that indicates connections between various components in a computer network being analyzed, data that identifies various components in the network, and other appropriate types of key performance indicators. In some implementations, indicators can include hospital admission rates, length of hospital stays, net income of a hospital, and a net promoter score (NPS) of a hospital. Indicators can have various formats, such as binary answers, e.g., yes or no in response to a condition, numerical values, free response text, or a combination of one or more of these.

The training engine 120 receives data for one or more entities from the data sources 122. The entities can be any appropriate types of entities, such as a business that implements a computer network, a person who has a home computer network, or another appropriate type of entity. The data sources 122 can be collated or processed in a way such that when the training engine 120 receives data from the data sources 122, the training engine 120 can use the received data as input data. For example, the training engine 120 can receive different types of data from different data sources 122 when the different types of data are for the same entity.

In some implementations, the training engine 120 creates a table for the data from the data sources 122. Creating a data table allows the training engine 120 to perform Boolean operations, e.g., build logic, using the data. While building the data table, the training engine 120 can perform data enrichment, e.g., look for missing entries in the data table and generate a request for more data from the data sources 122 or determine to auto-generate values for empty entries using machine learning.

In some implementations, the training engine 120 receives data that represents two or more indicators that include data indicating whether the entity performed at least one of the one or more actions. The training engine 120 can determine what properties in the data sources 122 correspond to indicators. For instance, the training engine 120 can receive first data that indications various components included in a computer network, second data that identifies one or more potential vulnerabilities for the computer network, and third data that indicates actions performed to reduce or eliminate the likelihood of the potential vulnerabilities.

In some implementations, the training engine 120 receives data from data sources 122 that represents two or more indicators that include data indicating whether a second entity performed at least one of the one or more actions. For example, the training engine 120 can receive first data from the entity, e.g., which maintains the computer network, and second data from a third party. The second data from the third party can be data from an external security vendor or auditor, data from a doctor or nurse when the entity is a patient, or data from another appropriate source, such as an information security entity or bug reporter. In some implementations, a human can verify whether the indicators identified by the training engine 120 are valid identifications.

The training engine 120 can create, or update, the node structures 101a and 101b using data from the data sources 122 as input data. The node structures 101a and 101b can be any appropriate type of node structure in which nodes can be added, removed, or both, links between nodes can be added, removed, or updated, or a combination of two or more of these. For instance, the node structure can be a decision tree or knowledge graph.

The training engine 120 can use the input data to determine the order of, connections between, or both, parent nodes 102a-d and leaf nodes 104a-e in the node structures 101a and 101b. The training engine 120 can create a node structure 101a-b for an indicator represented by at least some of the data from the data sources 122. For instance, the training engine 120 can identify an indicator, e.g., a key performance indicator, in the data and create a node structure 102a-b for the indicator.

Leaf nodes 104 represent an action that can be performed to adjust a value of the indicator. The parent nodes 102 are any node the node structure 101a-b that isn't a leaf node 104. All root nodes are also parent nodes 102. For example, the node structure 101a can include a root node, e.g., parent node 102a. Uni-directional links 108 connect a root node to parent nodes, e.g., parent node 102a to parent node 102b, root nodes to leaf nodes, e.g., parent node 102a to 104a, parent nodes to other parent nodes, e.g., parent node 102a to parent node 102b, and parent nodes to leaf nodes, e.g., parent node 102b to leaf node 104b.

The training engine 120, the recommendation engine 110, or both, can navigate from a parent node 102a to other parent nodes 102b or leaf nodes 104a, 104b, and 104f by determining whether or not a condition is met or satisfies some criteria, e.g., "does a patient smoke?" or "has this type of firewall ever been breached?". Parent nodes 102 can represent the values of indicators in the data sources 122. Links can allow the training engine 120 to start at a parent node 102 and arrive at a leaf node 104, so that the node structure can make a recommendation.

Uni-directional links 108 generally indicate a causal relationship. For example, node structure 101a can determine an appropriate medicine to prescribe a patient. Parent node 102a can represent the age of a patient, e.g., correspond to an age indicator. Uni-directional links 108 can determine what indicator for the training engine 120 to evaluate next. For example, if the patient is above fifty years of age, a uni-directional link 108 can allow the training engine 120 to navigate from parent node 102a to leaf node 104b, which can represent an action recommendation to prescribe medication A. If the patient is under fifty years of age, a uni-directional link 108 can connect parent node 102a to parent node 102b, which can represent the smoking history of the patient. If the patient has a smoking history, a uni-directional link can connect parent node 102b to leaf node 104f, which can represent an action recommendation to prescribe medication B. If the patient has no smoking history, a uni-directional link can connect parent node 102b to leaf node 104b, which can represent an action recommendation to not prescribe any medication.

In some implementations, the node structure 101b is a knowledge graph. The node structure 101b can include multiple bi-directional links 112, each of which connect one node with at least one other node in the node structure 101b. For instance, the node structure 101b includes a bi-directional link 112 that connects a parent node 102c with a parent node 102d.

Bi-directional links 112 can indicate general correlation between connected nodes, e.g., are not limited to a causal relationship. For example, parent node 102c can represent the satisfaction score of a hospital, and parent node 102d can represent enrollment at the hospital. If a hospital has a high satisfaction score, the hospital can be more likely to have a high enrollment score, since patients might encourage others to enroll given their high satisfaction. However, if a hospital has a low enrollment score, e.g., more patients are un-enrolling than enrolling, the enrolled patients might notice the diminishing number of patients and be more likely to become dissatisfied. Bi-directional links 112 can capture relationships, e.g., between parents nodes 102c and 102d, between indicators that influence each other.

Leaf nodes 104 can represent action recommendations, which can be at an end of the node structures 101a and 101b. In the node structure 101a, the training engine 120 might not be able to navigate any further once it has arrived at a leaf node 104. Leaf nodes 104 can represent action recommendations to improve network security or the health of the patient, reduce risk for the entity, or both.

Links can have varying strengths, related to the strength of the correlation or causal relationship between the combinations of parent nodes 102 and leaf nodes 104. For example, in the node structure 101a, a uni-directional link 108 can represent a likelihood that a first node affects a second node when the uni-directional link 108 goes from the first node to the second node. For instance, the uni-directional 108 like can indicate with what certainty a condition will affect the correct, next node. For example, the data sources 122 can include data that indicates a doctor prescribed medication B whenever a patient was under fifty years of age and/or the patient had a smoking history. In such an example, the uni-directional links 108 connecting parent nodes 102a and 102b and parent node 102b to leaf node 104f can have a strong relationship, e.g., being weighted more heavily. Bi-directional links 112 can also have varying strength and weights, e.g., age and height being strongly correlated for children, but not adults. The strength of the links can change over time, e.g., depend on the time of the year or age of the patient.

Given the data sources 122 containing indicators related to the security of an entity or an entity's computer network, actions taken to improve the security, and the results of the actions taken to improve the security, the node structures 101a and 101b can reflect which indicators have the strongest influence on the results of the actions taken to improve the security. Using the node structures 101a and 101b, the recommendation engine 110 can discover correlations between particular indicators and actions with respect to a particular result of actions taken to improve the security given the particular indicators for the entity.

The training engine 120 can determine what indicators from the input data should be parent nodes 102 in the structure. For example, some indicators can be deemed irrelevant for navigating to an appropriate leaf node 104, e.g., the input data could contain indicators for patient or device names, which do not influence action recommendations made to improve the health of the patients or network security.

In some examples, when the training engine 120 receives data from the data sources 122 for multiple entities, the training engine 120 can determine what indicators from the input data should be parent nodes 102 given a frequency with which correlations exist. For instance, the training engine 120 can determine that, for a given set of indicators, one or more actions improved performance, e.g., improved security. The training engine 120 can analyze the data from the data sources 122 to identify multiple entities that have the given set of indicators. The training engine 120 can determine, from the multiple entities, the percentage of entities that have the one or more actions that improved performance. When the percentage satisfies a percentage threshold, the training engine 120 can determine that the corresponding indicators should be parent nodes 102.

The percentage threshold can be any appropriate value. For example, the percentage threshold can be specific to an entity for which data was received, the multiple entities for which the training engine 120 received data from the data sources 122, or another appropriate entity or combination of entities.

In some implementations, the training engine 120 can analyze data from the data sources to determine a likelihood that certain indicators are correlated with actions performed by or for the corresponding entity. For instance, the training engine 120 can determine that a first indicator is not likely correlated with any actions performed by or for an entity and to not represent the first indicator with a parent node in the node structure 101a or 101b. The training engine 120 can determine that a second indicator is likely correlated with at least one action performed by or for an entity and to represent the second indicator with a parent node 102 in the node structures 101*a* and 101*b*.

The training engine 120 can determine an order of the parent nodes 102 in the node structure 101*a* and 101*b*, e.g., to optimize the node structure for making appropriate action recommendations. For example, if the purpose of a node structure 101*a* is to reduce hospitalizations or improve network security, some indicators, such as age or software update status, can better predict risk for a corresponding entity than other indicators. Accordingly, the training engine 120 can organize the node structure 101*a* to have a parent node 102*a* related to age earlier, rather than later, in the node structure.

In some examples, when determining the order of the parent nodes, the training engine 120 can assign weights to various ones of the parent nodes 102*a-d*, leaf nodes 104*a-f*, uni-directional links 108, bi-directional links 112, or combination of more than one. For instance, the training engine 120 can determine weights for the nodes such that the recommendation engine 110 analyzes nodes with higher weights before analyzing nodes with lower weights. The training engine 120 can determine weights for uni-directional links 108 and bi-directional links 112 to cause the recommendation engine 110 to traverse the node structure 101*a* or 101*b* down a particular path given the combination of indicators for a particular entity. Each path would be different for a different entity that has a different combination of indicators.

In some implementations, the training engine 120 can use an impurity function, which measures the success of the training engine 120 in properly navigating from a parent node 102 to an appropriate, final leaf node 104. If the training engine 120 can navigate from a parent node 102 to an appropriate leaf node 104 correctly given a set of input data, that parent node 102 has zero impurity. For example, input data can contain multiple indicators, previous actions taken to improve performance, and the results of the actions taken to improve performance. If the training engine 120 correctly navigates from a parent node 102*a*, e.g., a node indicating whether an entity has blood pressure above the threshold amount or whether a computer network device had a firewall installed, to the correct, final leaf nodes 104*a*, 104*b*, or 104*f*, e.g., nodes representing action recommendations to prescribe or not prescribe the entity medication or a type of firewall to install, that parent node 102*a* has zero impurity.

A parent node 102 can have nonzero impurity if the training engine 120 only sometimes navigates to the correct, final leaf nodes 104. For example, the training engine 120 might not be able to correctly predict, given a parent node 102*a*, e.g., a node determining the marital status of an entity, the appropriate final leaf node 104, an action recommendation to prescribe or not prescribe the entity medication. In this case, the parent node 102*a* would have nonzero impurity. Various functions, such as Gini impurity, information gain, and variance reduction, can be used as impurity functions. When a parent node has nonzero impurity, the training engine 120 can determine to not include the indicator for the parent node in the node structure 101*a* or 101*b*, to not include a link between the parent node and the final leaf nodes for which there is nonzero impurity, to reduce a likelihood that the recommendation engine 110 will traverse the node structure 101*a* or 101*b* from the parent node to the final leaf nodes for which there is nonzero impurity, e.g., using corresponding weights, or a combination of two or more of these.

The training engine 120 can create, destroy, update, or a combination of these, uni-directional links 108 and bi-directional links 112 between nodes representing indicators if doing so improves the performance of the node structures 101*a* and 101*b*. For example, the training engine 120 can receive input data that represents two or more indicators of an entity. The indicators of the entity can identify one or more actions performed for the entity and the training engine 120 can determine, using the input data, whether the two or more indicators together reduced risk for the entity.

The training engine 120 can determine, for a node structure 101*a* or 101*b* that includes multiple parent nodes 102 that each represent a corresponding indicator and multiple leaf nodes 104 that each indicate an action to perform, whether the node structure includes a link between the multiple indicators and each of the multiple actions by accessing and or using the input data. In response to determining that the node structure does not include the link, the training engine 120 can create a link between a nodes in the various node structures 101*a-b*. For instance, the training engine 120 can create a link between parent node 102 and leaf node 104, for which the link did not previously exist. In some implantations, the training engine 120 can create a link between parent nodes 102, between leaf nodes 104, or both.

In some implantations, the training engine 120 can create a link between node structures before completing training of the node structure. For example, the training engine 120 can determine, for an indicator that indicates actions performed by a first entity, whether a node structure 101*a*, e.g., a first tree structure, for the indicator includes a link with another node structure 101*b*, e.g., a second tree structure, for a second indicator. In response to determining that node structure 101*a* does not include a link with the node structure 101*b*, the training engine 120 can determine a weight for a link 114 between the first tree structure and the second tree structure and create the link 114 between the node structure 101*a* and the node structure 101*b* that includes the weight. In some implementations, the link 114 can be uni-directional or bi-directional. In this example, link 114 connected leaf node 104*b* and parent node 102*c*, turning leaf node 104*b* into a parent node 102*e* and node structures 101*a* and 101*b* into a single, updated node structure 101*c*. In some implementations, link 114 connects parent nodes to each other, leaf nodes to each other, root nodes to each other, non-root nodes to each other, a root node to a non-root node, a parent node to a leaf node, or a combination of more than one of these.

The training engine 120 can maintain, in memory, the updated node structure 101*c* that includes the link 114 for use in generating, using two or more second indicators for another entity, a recommendation of an action to reduce risk for the other entity. In this way, the environment 100 can update the node structure using historical data from the data sources 122 to improve future recommendations for other entities.

The training engine 120 can create links between nodes in the node structures 101*a* and 101*b* for indicators that are also recommendations, e.g., action recommendations. For instance, the input data can include first data that represents an initial recommendation for the entity and second data that represents an indicator of the entity. The training engine 120 can determine whether the node structure includes a link between the two or more indicators by determining whether the node structure includes a link between the initial recommendation for the entity and a node for the indicator of the entity. In this specification, reference to an indicator in the node structure refers to reference of a node that represents the indicator.

In response to determining that the node structure does not include the link between the initial recommendation and the indicator, the training engine 120 can create the link between the initial recommendation and the indicator. In some implementations, node structure includes a first parent node that represents the initial recommendation and a second parent node that represents the indicator. In this way, the training engine 120 can determine correlations between various indicators that include initial action recommendations to determine an optimal action recommendation given the input data. As a result, the recommendation engine 110 can determine whether to provide the initial recommendation as an action recommendation, potentially along with other action recommendations, or to only provide other action recommendations and to skip providing the initial recommendation. The latter can occur when the other action recommendations are optimal and supersede the initial recommendation.

In some implementations, the training engine 120 can connect nodes when an entity has multiple action recommendations. For example, a training engine 120 can generate a first node structure that results in a first recommendation for the entity and a second node structure that results in a second recommendation for the entity, e.g., arriving at both leaf nodes 104*f* in node structure 101*a* and 104*e* in node structure 101*b*. The training engine 120 can determine whether the node structures 101*a* and 101*b* include a link between the first and second recommendations for the entity. In response to determining that the node structure does not include the link, the training engine 120 can create the link between the two action recommendations. In some implementations, the training engine 120 can create links between action recommendations within a single node structure.

In some implementations, after the training engine 120 updates the node structure when an entity has multiple action recommendations, the recommendation engine 110 can access, for another entity, the updated node structure 101*c* using multiple indicators for the other entity. The recommendation engine 110 can generate, using the updated node structure 101*c* that represents multiple positive correlations between the two or more second indicators for the second entity and the first recommendation and the second recommendation, a recommendation of an action to reduce risk for the other entity. In such an instance, the recommendation engine 110 can use more than one action recommendation to generate a single action recommendation.

In some implementations, the training engine 120 can maintain the updated node structure 101*c*, send the updated node structure 101*c*, e.g., to the recommendation engine 110, or both. For instance, the training engine 120 can maintain, in memory, the updated node structure 101*c* that includes a generated link.

The training engine 120 can provide a trained, updated node structure 101*c* to the recommendation engine 110. The recommendation engine 110 can receive the trained, updated node structure 101*c* from the training engine 120.

The recommendation engine 110 can receive a request for a recommendation from a user device 130. The request can be for or identify a particular entity. In some examples, the recommendation engine 110 can receive the request and then determine the particular entity using data included in the request, e.g., data that indicates an account for the user device 130.

The request can include data for indicators 134 for the particular entity. The data can indicate the indicators 134 or can be a reference to the indicators. In some examples, when the data references the indicators, the data can be a key included in the request. The recommendation engine 110 can use the key to determine the indicators for the particular person, e.g., by using the key when accessing a database.

The recommendation engine 110 can use the indicators 134 to determine one or more action recommendations for the particular entity. For instance, the recommendation engine 110 can use the indicators 134 to traverse the updated node structure 101*c* to determine action recommendations given the indicators 134 for the particular entity. The recommendation engine 110 can determine, using the updated node structure 101*c*, the action recommendations 138 that are most likely to reduce risk for the particular entity, improve performance of the particular entity, or both.

When the updated node structure 101*c* includes uni-directional links 108 and bi-directional links 112, that each have corresponding weights, the recommendation engine 110 can use the weights to traverse the updated node structure 101*c*. For instance, the updated node structure 101*c* can determine a node for one of the indicators 134. The recommendation engine 110 can determine which link connected to the node has a highest weight given the combination of the indicators 134. The recommendation engine 110 can use the link to traverse the updated node structure 101*c*, similarly accessing other parent nodes 102 in the updated node structure 101*c* until the recommendation engine 110 determines that all appropriate leaf nodes 104 have been identified. The recommendation engine 110 can use a threshold to determine whether all appropriate leaf nodes 104 have been identified. The recommendation engine 110 can then use the action recommendations for the identified leaf nodes 104.

In some implementations, the recommendation engine 110 can receive a request after the training engine 120 has created a link between at least one of two or more indicators and another action that was not included in the initial node structure 101*a* or 101*b*. The link can be between multiple nodes, each of which can represent an initial one or more actions. When the indicators 134 indicate that the one or more actions were performed for the particular entity, the recommendation engine 110 can determine to generate an action recommendation 138 for the particular entity. In response to determining to generate the recommendation, the recommendation engine 110 can access the updated node structure 101*c* using the two or more indicators for the entity. The recommendation engine 110 can generate, using the updated node structure 101*c*, an action recommendation 138 for the other action, which was not included in the one or more actions performed for the entity, to reduce risk for the entity.

The recommendation engine 110 can provide the appropriate action recommendation 138 to the user device 130. For instance, the recommendation engine 110 can generate instructions that, when received by the user device 130, cause the user device to present a unified user interface 132. The unified user interface 132 can depict one or more action recommendations 138 and the indicators 134. The unified user interface 132, such that all of the indicators 134 and action recommendations 138 are presented in a single user interface.

For instance, in contrast to other systems that receive data from the various data sources 122 and present data from a data source in a respective user interface, the user device 130 can present the indicators 134 received from the different data sources 122 in the unified user interface 132. Along with the presentation of the indicators that were received from the different data sources 122, the user device 130 can present, in the unified user interface 132, the one or more action recommendations 138. By generating the unified user interface 132, the user device 130 can reduce an amount of computational resources that would be required for generation of separate user interfaces for indicators received from different ones of the data sources 122. By generating the unified user interface 132, the user device can reduce or eliminate an amount of computational resources required to switch between different user interfaces that present indicators from various ones of the data sources 122.

In some implementations, the recommendation engine 110 can generate an action recommendation 138 that the user device 130, or another component in a system, automatically implements. For instance, the recommendation engine 110 can generate an action recommendation 138 to install a software update. The recommendation engine 110 can provide the action recommendation 138 to the user device 130 to cause the user device 130 to implement the action recommendation, e.g., to install the software update, without the user device 130 presenting the action recommendation 138, e.g., on a display.

In some implementations, indicators can relate to the health of an entity, such as medical history, a risk score of an upcoming threat to health associated with an entity, previous actions taken to improve the health of the patient, the results of actions performed to improve the health of the patient, e.g., reduced risk scores following a performed action, and other medical data.

When the environment 100 includes a node structure for health data, the data sources 122 can include data for other types of key performance indicators. For instance, the key performance indicators can include, for a patient, whether the patient smokes, the patient's age, the patient's weight, whether the patient was recently admitted to a hospital, or whether the patient received preventative care.

Given the data sources 122 containing indicators related to the health of an entity, actions taken to improve the health of the entity, and the results of the actions taken to improve the health of the entity, the node structure can reflect which indicators have the strongest influence on the results of the actions taken to improve the health of the entity.

In some implementations, data sources 122 include, but are not limited to, health information exchange (HIE) data, payer data, Center for Medicare & Medicaid Services (CMS) data, third party vendor data, internal application data, patient health information data, operational data, and financial data.

The components in the environment 100 can be examples of systems or subsystems implemented as computer programs on one or more computers in one or more locations, in which the systems, components, and techniques described in this specification are implemented. The user devices 130 can include personal computers, mobile communication devices, and other devices that can send and receive data over a network. The network (not shown), such as a local area network ("LAN"), wide area network ("WAN"), the Internet, or a combination thereof, connects the user devices 130, the recommendation engine 110, the training engine 120, and the data sources 122.

The environment 100 can include several different functional components, including the recommendation engine 110 and the training engine 120. The recommendation engine 110, the training engine 120, or a combination of these, can include one or more data processing apparatuses, can be implemented in code, or a combination of both. For instance, each of the recommendation engine 110 and the training engine 120 can include one or more data processors and instructions that cause the one or more data processors to perform the operations discussed herein.

The various functional components of the environment 100 can be installed on one or more computers as separate functional components or as different modules of a same functional component. For example, the recommendation engine 110 and the training engine 120 of environment 100 can be implemented as computer programs installed on one or more computers in one or more locations that are coupled to each through a network. In cloud-based systems for example, these components can be implemented by individual computing nodes of a distributed computing system.

Figure 2B:
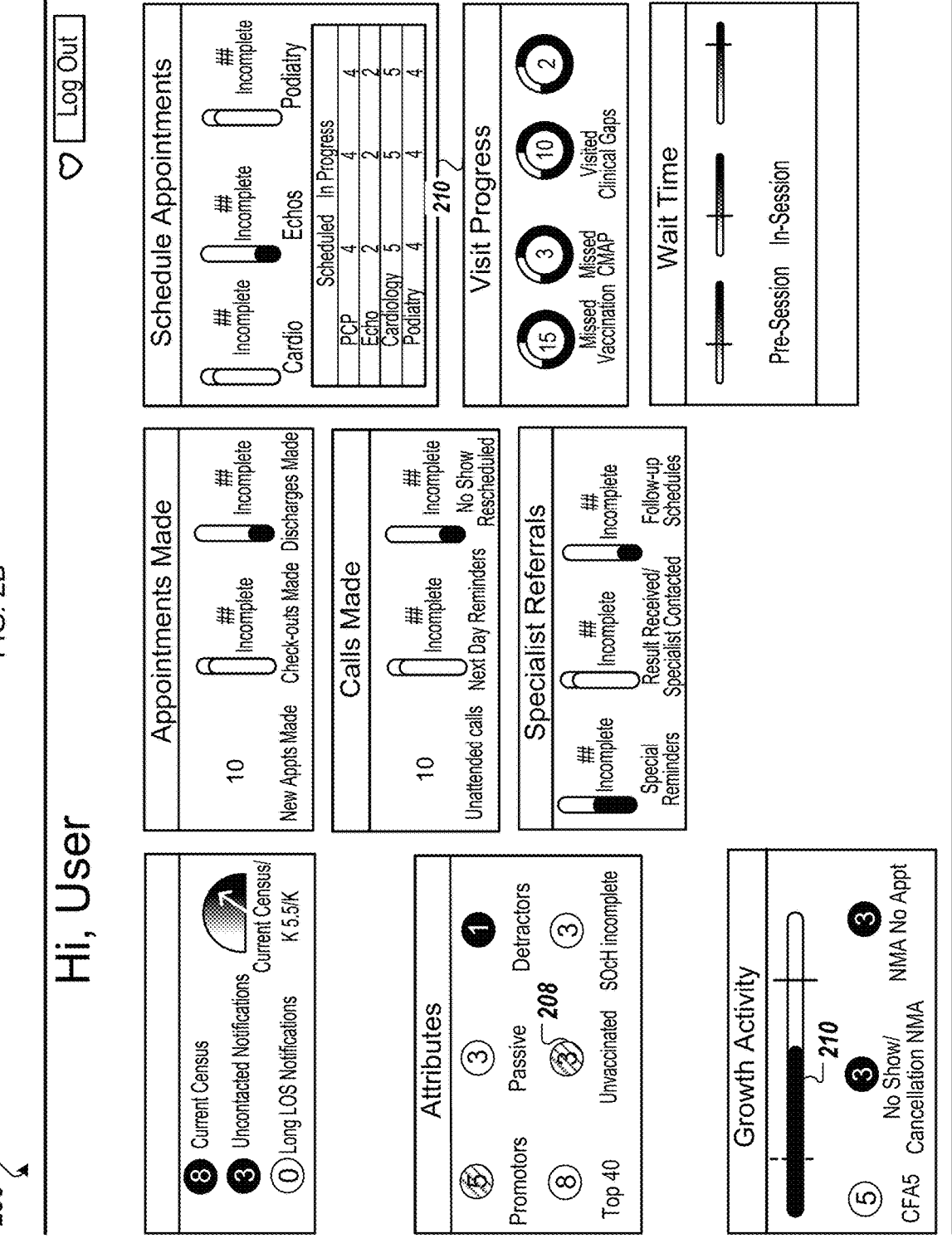

FIGS. 2A-B depict an example of unified user interface 200. For ease of explanation, the example unified user interface 200 has been split into two figures. In some implementations, the user interface can have icons 202 that enable navigation between different tabs in the unified user interface 200. FIG. 2A depicts a unified user interface 200 on the "My Center" tab, as indicated by the bold, underlined text. As part of the My Center tab, the unified user interface 200 can present news 204 and general announcements for a user associated with a user device 130 that generates the unified user interface 200.

The unified user interface 200 can present a checklist with represents action recommendations 206 for the user associated with the user device 130. This checklist can indicate one or more actions recommendations for the user to perform. The action recommendations can be for a specific entity, e.g., the user or a patient with whom the user is working or a business with whom the user is working. The unified user interface 200 can enable the user to filter the checklist in unique ways, e.g., by patient, initiative, etc.

The direct connection between the unified user interface 200 and the recommendation engine can reduce an amount of time between the recommendation engine generating an action recommendation 206 and the unified user interface 200 presenting the action recommendation 206. Quick presentation of the action recommendation 206 can increase the chance of implementation of the action recommendation 206 in a timely manner. The order of the action recommendations 206 can be arranged to reflect the priority of the action recommendations 206, e.g., be based on a health risk score of the patient associated with the action recommendation 206.

The action recommendations 206 can relate to various indicators displayed on the unified user interface 200. Icons can represent indicators with various visual symbols. For example, with reference to FIG. 2B, the number on an icon 208 or how much of a bar icon 210 is filled can represent the absolute value of an indicator. The color or pattern on an icon 208 can represent the trend, e.g., currently increasing or decreasing, of an indicator. In some implementations, the unified user interface 200 can present graphs to represent past and present values of indicators.

In some implementations, the action recommendations 206 can represent a difference between a value, e.g., an indicator, for an entity, e.g., a health care provider, and a trend line for a type of the value. For instance, when the value is for a goal for the entity, the recommendation engine 110 can generate the action recommendation 206 that represents a difference between the goal for the entity and historical data for the goal for the entity. The action recommendation 206 can indicate one or more actions for the entity to increase a likelihood that the entity achieves the goal.

The unified user interface 200 can include a tab, e.g., the "Explore Core Models" tab, which presents in the unified user interface 200, information about how the recommendation engine 110 generates action recommendations 206. In some implementations, the unified user interface 200 can present a representation of the node structure, links between indicators in the node structure, or both. For instance, the unified user interface 200 can present data that indicates correlations found between various indicators, which correlations are represented by the links between the indicators.

In some implementations, the unified user interface 200 can report what links the training engine created given data for a particular entity, in response to a user request for an action recommendation 206, or both. In some implementations, the user has access to the node structure through the unified user interface 200 and can detect correlations between indicators through a visualized node structure.

The unified user interface 200 can be organized in a way to reduce eyestrain for the user, e.g., utilize pop-ups and collapsible windows to present information on demand rather than all at once, present information using color and graphs instead of lengthy text to convey the same information. The unified user interface 200 can emphasize action recommendations 206 or use visual cues to highlight icons 208 and 210 that relate to performance metrics that relate to the action recommendation 206.

In some implementations, the unified user interface 200 can notify the user when an entity, e.g., a patient, has more than one or conflicting associated action recommendations 206. Such a notification can be useful when dealing with complex problems, such as medical issues. For example, when the recommendation engine generates an action recommendation that is different from one or more initial recommendations for the particular entity, the recommendation engine can determine whether the initial recommendations should be provided alone with the action recommendation. When the recommendation engine determines to provide the initial recommendations with the action recommendation, the recommendation engine can determine whether the initial recommendations should likely be performed with the action recommendation. For instance, the recommendation engine can determine a likelihood that an initial recommendation would reduce risk, improve performance, or both, given the action recommendation. If the likelihood satisfies a likelihood threshold, the recommendation engine can provide the initial recommendation with the action recommendation. If the likelihood does not satisfy the likelihood threshold, the recommendation engine can determine to skip providing the initial recommendation.

The likelihood threshold can be any appropriate value. In some examples, the recommendation engine can select the likelihood threshold using the entity for which a recommendation is being generated, one or more entities whose data was used to create one or more links in the tree structure, which links were used to generate the action recommendation, or a combination of both.

The unified user interface 200 can include windows to allow the user to provide feedback about the unified user interface 200 and action recommendations 206.

In some examples, when the likelihood does not satisfy the likelihood threshold, the recommendation engine can provide data about the initial recommendation with the action recommendation. The data can indicate why the likelihood does not satisfy the likelihood threshold, e.g., data from the node structure that indicates a frequency with which performance of the initial recommendation reduced risk, improved performance, or both.

FIG. 3 is a flow diagram of an example process 300 for using a node structure for action recommendations. For example, the process 300 can be used by the training engine 120 and recommendation engine 110 from the environment 100. In some implementations, the first mentioned entity can be a patient, health care provider, or network whose data is used to train the node structure, and the other entity can be a patient or network about whom the recommendation engine will generate a new recommendation. The first and second entities can be different entities.

A training engine 120 can maintain, in memory and for each of two or more indicators of a first entity, a corresponding tree structure that identifies the corresponding indicator and one or more attributes that affect the indicator (310). The tree structure can have multiple parent nodes, each of which represent indicators that are not actionable for the first entity. The tree structure can also have multiple leaf nodes, each of which represent an action that can be performed for the first entity to adjust a value of the indicator In some implementations, the indicators of the entity can identify one or more actions performed for the entity that together reduced risk for the entity. For example, the training engine 120 can benefit from having examples of a patient or computer network with reduced risk after specific actions were performed. The data can represent the reduced risk using a risk score that represents a likelihood of risk, an improved performance, or both.

In some implementations, each root node in the tree structures can represent a key performance indicator.

The training engine 120 can determine, for a first indicator from the multiple indicators and using data that indicates actions performed for the first entity, whether a first tree structure for the first indicator includes a link with a second tree structure for a second indicator from the multiple indicators (320). For example, a training engine can determine that two indicators are correlated with risk of hospitalization, but the relevant indicators and actions can lack a link. The actions can be performed by the first entity, e.g., an employee of the first entity. The actions can be performed by another person and for the first entity, e.g., by a patient performing an action recommended by the first entity.

The training engine 120 can determine a weight for a link between the first tree structure and the second tree structure (330). The determination of the weight can be responsive to determining that the first tree structure does not include the link with the second tree structure.

In some implementations, determining the weight can include determining that the weight that indicates an amount by which one or more nodes in the second tree structure affect the value of the first indicator. For example, when indicators and actions are correlated, linking those indicators can improve the performance of the node structure.

The training engine 120 can create the link between the first tree structure and the second tree structure that includes the weight (340). In some implementations, the training engine 120 creates uni-directional links 108, bi-directional links 112, or both. The link can connect any combination of parent, leaf, root, or non-root nodes.

In response to determining that the first tree structure does not include the link with the second tree structure, the training engine 120 can determine to skip creating a link between the two or more indicators and an action from the one or more actions. For example, given that the indicators and actions are correlated, and a link already exists, the training engine 120 can determine to maintain the link in the node structure.

In some examples, the training engine 120 can determine that there is not a correlation between two or more indicators for which the node structure includes a link between corresponding nodes for the two or more indicators. This can occur when there was previously a correlation between an indicator and an initial recommendation, between two indicators, or both. The training engine 120 can determine to remove the link between the two or more indicator for which there is not a correlation.

The training engine 120 can maintain, in memory, the first tree structure, the second tree structure, and the link between the first tree structure and the second tree structure that includes the weight. The training engine 120 can use the first tree structure, the second tree structure, and the link to generate a recommendation of an action to adjust a value of the first indicator for an entity (350). In some implementations, the action can include an automated action performed automatically by a system, actions performed to reduce a risk of readmission by the first entity to a hospital, or both.

In some implementations, memory can store the node structure until a recommendation engine receives a request. Then the training engine 120 can provide the node structure to the recommendation engine 110 for use generating the recommendation.

In some examples, the recommendation engine 110 might receive a single subset that includes the second data. The first subset of second data can indicate input in a user interface of at least one of the two or more second indicators of the other entity. The second subset of second data can represent at least one of the two or more second indicators of the other entity. In some implementations, the second subset of second data is received from a database different from the device that sent the first subset of second data. The data received in this step can be related to a request for an action recommendation or display of indicators related to an entity. The device can be one of the one or more devices. In some examples, the device is a different device not included in the one or more devices.

The order of steps in the process 300 described above is illustrative only and can be performed in different orders. For example, steps 320, 330, and 340 can repeat more than once before advancing to step 350. In those instances, the accuracy of a node structure can benefit from the addition of more than one additional link, e.g., for generation of more accurate action recommendations.

In some implementations, the process 300 can include additional steps, fewer steps, or some of the steps can be divided into multiple steps. For example, in some implementations, the training engine 120 can provide the updated node structure to the recommendation engine in addition to or instead of maintaining the updated node structure in memory.

In some implementations, the training engine 120 can determine a second weight that indicates an amount by which multiple nodes in the first tree structure affect the second indicator. The weight can indicate an amount by which one or more nodes in the second tree structure affect the first indicator. In such implementations, creating the link can include creating the link that includes the first and second weight.

In some implementations, the training engine 120 can maintain, for each of the multiple indicators for the first (second) entity, a first (second) set of weights for nodes in the corresponding tree structure. The training engine 120 can determine, for the first (second) entity and using the first (second) set of weights, a first (second) recommendation of a first (second) action to adjust a value of the first (second) indicator for the first entity. The first and second entities, sets of weights, recommendations, and indicators can be different.

In some implementations, the recommendation engine 110 can receive, from a device, a first subset of second data indicating input in a user interface of at least one of two or more second indicators of another entity. The recommendation engine 110 can receive, from a database different from the device, a second subset of the second data that represents at least one of the two or more second indicators of the other entity. The recommendation engine 110 can determine, using the link between the first tree structure and the second tree structure and the two or more second indicators of the other entity, the recommendation of the action to reduce risk for the other entity. The recommendation engine 110 can provide, to the device, second data for the recommendation to cause the device to present, using the second data, the recommendation in the user interface.

In such implementations, the recommendation engine 110 can receive data from the database different from the device, the second subset of the second data that represents the at least one of the two or more second indicators of the other entity. Providing the second data can include providing the second data for the recommendation to cause the device to present, in a unified user interface, the recommendation and at least two of the two or more second indicators of the other entity. The at least two of the two or more second indicators can include a first indicator received from the device and a second indicator received from the database different from the device.

In some implementations, the presentation is in a unified user interface. In some implementations, the user input can contain requests for multiple entities and action recommendations. In some implementations, the generated action recommendations and indicators can relate to more than one entity, e.g., a group of patients or networks.

In some implementations, the training engine 120 can receive first data that represents an initial recommendation for the first entity and second data that represents an indicator of the first entity. Determining whether the first tree structure includes a link with the second tree structure can include determining whether the tree structures for the two or more indicators include a link between the initial recommendation for the first entity and the indicator of the first entity. Creating the link can include, in response to determining that the tree structures for the two or more indicators do not include a link between the initial recommendation and the indicator, creating the link between the initial recommendation and the indicator. The initial recommendation and the indicator can each be in separate ones of the first tree structure and the second tree structure.

In such implementations, the second tree structure can include a first parent node that represents the initial recommendation, and the first tree structure can include a second parent node that represents the indicator.

In some implementations, creating the link can include, in response to determining that the tree structures for the two or more indicators do not include the link between the first recommendation and the second recommendation, creating the link between the first recommendation in the first tree structure and the second recommendation in the second tree structure.

In such implementations, the training engine 120 can access, for another entity, the link between the first tree structure and the second tree structure using two or more second indicators for the other entity. The training engine 120 can generate, using the link between the first tree structure and the second tree structure that represents one or more positive correlations between a) the two or more second indicators for the other entity and b) the first recommendation and the second recommendation, a recommendation of an action to reduce risk for the other entity.

In some implementations, step 330 can be broken up into two steps, the first step involving determining the weight for the link, and the second step involving creating the link. These two steps can occur in either order, e.g., determining the weight before creating or vice versa.

Personally identifiable information related to patients isn't necessarily included in data received from the data sources. HIPPA and patient-provided consent will inform how and when personally identifiable data is stored and supplied to the user interface. In addition, certain data may be anonymized in one or more ways before it is stored or used, so that personally identifiable information is removed. For example, a user's identity may be anonymized so that no personally identifiable information can be determined for the user, or a user's geographic location may be generalized where location information is obtained (such as a city, ZIP code, or state level), so that a particular location of a user cannot be determined. Thus, the user may have control over how information is collected about him or her and used by the training engine, the recommendation engine, or both.

A number of implementations have been described. Nevertheless, it will be understood that various modifications may be made without departing from the spirit and scope of the disclosure. For example, various forms of the flows shown above may be used, with steps re-ordered, added, or removed.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a smart phone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks;

and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., LCD (liquid crystal display), OLED (organic light emitting diode) or other monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an Hypertext Markup Language (HTML) page, to a user device, e.g., for purposes of displaying data to and receiving user input from a user interacting with the user device, which acts as a client. Data generated at the user device, e.g., a result of the user interaction, can be received from the user device at the server.

Figure 4:
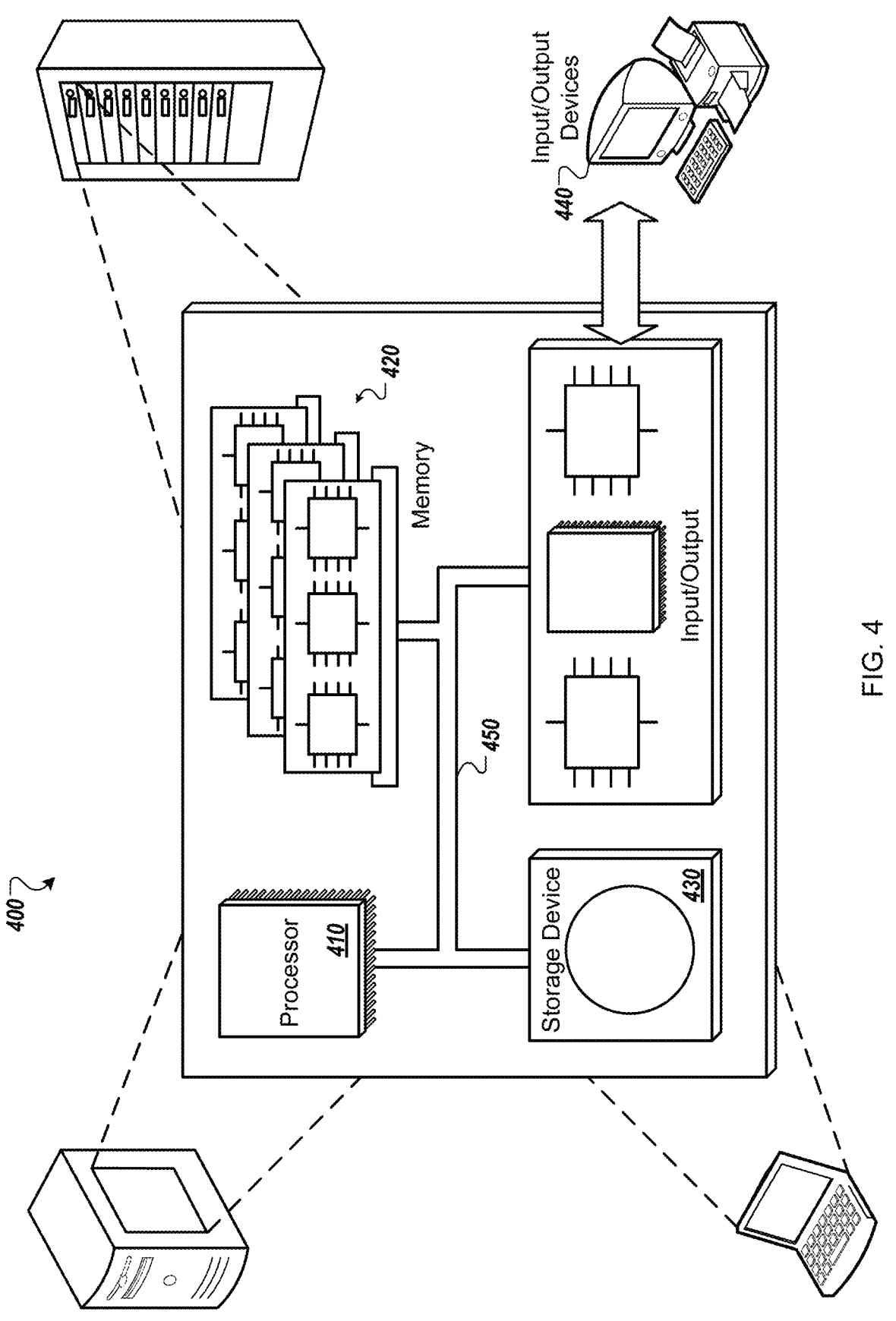
FIG. 4 is a block diagram of a computing system that can be used in connection with computer-implemented methods described in this specification.

An example of one such type of computer is shown in FIG. 4, which shows a schematic diagram of a computer system 400. The system 400 can be used for the operations described in association with any of the computer-implemented methods described previously, according to one implementation. The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the system 400. In one implementation, the storage device 430 is a computer-readable medium. In various different implementations, the storage device 430 may be a floppy disk device, a hard disk device, an optical disk device, or a tape device.

The input/output device 440 provides input/output operations for the system 400. In one implementation, the input/output device 440 includes a keyboard and/or pointing device. In another implementation, the input/output device 440 includes a display unit for displaying graphical user interfaces.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims, described in the specification, or depicted in the figures can be performed in a different order and still achieve desirable results. In some cases, multitasking and parallel processing may be advantageous.

What is claimed is:

1. A computer-implemented method comprising:

receiving a request comprising two or more indicators of a first entity, the two or more indicators comprising a first indicator and a second indicator;

maintaining, in memory and for the first indicator, a first tree structure that identifies the first indicator and one or more first attributes that affect the first indicator, the first tree structure having i) one or more first parent nodes each of which represent indicators that are not actionable for the first entity and ii) one or more first leaf nodes each of which represent an action that can be performed for the first entity to adjust a value of the first indicator;

maintaining, in the memory and for the second indicator, a second tree structure that identifies the second indicator and one or more second attributes that affect the second indicator, the second tree structure having i) one or more second parent nodes each of which represent indicators that are not actionable for the first entity and ii) one or more second leaf nodes each of which represent an action that can be performed for the first entity to adjust a value of the second indicator;

determining, for the first indicator and using data that indicates actions performed for the first entity, whether the first tree structure for the first indicator includes a link with the second tree structure;

in response to determining that the first tree structure does not include the link with the second tree structure:

determining a weight for a link between the first tree structure and the second tree structure; and creating the link between the first tree structure and the second tree structure that includes the weight; and maintaining, in the memory, the first tree structure, the second tree structure, and the link between the first tree structure and the second tree structure that includes the weight for use in generating, using the second tree structure and the link that includes the weight, a recommendation of an action to adjust a value of the first indicator for an entity.

2. The method of claim 1, wherein determining the weight comprises determining the weight that indicates an amount by which the one or more second parent nodes and the one or more second leaf nodes in the second tree structure affect the value of the first indicator.

3. The method of claim 1, wherein creating the link comprises creating a bi-directional link between the first tree structure and the second tree structure.

4. The method of claim 3, the method comprising:

determining a second weight that indicates an amount by which the one or more first parent nodes and the one or more first leaf nodes in the first tree structure affect the second indicator, wherein:

the weight indicates an amount by which the one or more second parent nodes and the one or more second leaf nodes in the second tree structure affect the first indicator; and creating the link comprises creating the link that includes the weight and the second weight.

5. The method of claim 1, wherein creating the link comprises creating a link between a first root node of the first tree structure and a second root node of the second tree structure.

6. The method of claim 1, wherein creating the link comprises creating a link between a first root node of the first tree structure and a second non-root node of the second tree structure.

7. The method of claim 1, comprising:

maintaining, for each of the first indicator and the second indicator, a first set of weights for nodes in the first tree structure and the second tree structure, respectively;

maintaining, for each of two or more indicators for a second different entity, a second different set of weights for nodes in a corresponding tree structure;

determining, for the first entity and using the first set of weights, a first recommendation of a first action to adjust a value of the first indicator for the first entity; and determining, for the second different entity and using the second different set of weights, a second recommendation of a second different action to adjust a value of an indicator of the two or more indicators for the second different entity.

8. The method of claim 1, wherein the action comprises an automated action performed automatically by a system.

9. The method of claim 1, wherein the first tree structure comprises a first root node, the second tree structure comprises a second root node, the first root node represents a first key performance indicator, and the second root node represents a second key performance indicator.

10. The method of claim 1, wherein the first entity comprises a patient or a health care provider.

11. The method of claim 1, wherein the one or more actions comprise actions performed to reduce a risk of readmission by the first entity to a hospital.

12. The method of claim 1, comprising:

receiving, from a device, a first subset of second data indicating input in a user interface of at least one of two or more second indicators of another entity;

receiving, from a database different from the device, a second subset of the second data that represents at least one of the two or more second indicators of the other entity;

determining, using the link between the first tree structure and the second tree structure and the two or more second indicators of the other entity, the recommendation of the action to reduce risk for the other entity; and providing, to the device, second data for the recommendation to cause the device to present, using the second data, the recommendation in the user interface.

13. The method of claim 12, wherein receiving the second subset of the second data comprises receiving, from the database different from the device, the second subset of the second data that represents the at least one of the two or more second indicators of the other entity.

14. The method of claim 12, wherein providing the second data comprises providing the second data for the recommendation to cause the device to present, in a unified user interface, the recommendation and at least two of the two or more second indicators of the other entity, the at least two of the two or more second indicators comprising a first indicator received from the device and a second indicator received from the database different from the device.

15. The method of claim 1, comprising:

receiving first data that represents an initial recommendation for the first entity and second data that represents an indicator of the two or more indicators of the first entity, wherein:

determining whether the first tree structure includes a link with the second tree structure comprises determining whether the first tree structure and the second tree structure include a link between the initial recommendation for the first entity and the indicator; and creating the link comprises, in response to determining that the first and second tree structures for the two or more indicators do not include a link between the initial recommendation and the indicator, creating the link between the initial recommendation and the indicator, wherein the initial recommendation and the indicator are each in separate ones of the first tree structure and the second tree structure.

16. The method of claim 15, wherein the one or more second parent nodes of the second tree structure comprise a first parent node that represents the initial recommendation and the first tree structure comprises a second parent node that represents the indicator.

17. The method of claim 1, comprising:

receiving first data that represents a first recommendation for the first entity and second data that represents a second recommendation for the first entity, wherein:

determining whether the first tree structure includes a link with the second tree structure comprises determining whether the first tree structure and the second tree structure for the two or more indicators include a link between the first recommendation for the first entity and the second recommendation for the first entity; and creating the link comprises in response to determining that the first tree structure and the second tree structure do not include the link between the first recommendation and the second recommendation, creating the link between the first recommendation in the first tree structure and the second recommendation in the second tree structure.

18. The method of claim 17, comprising:

accessing, for another entity, the link between the first tree structure and the second tree structure using two or more second indicators for the other entity; and generating, using the link between the first tree structure and the second tree structure that represents one or more positive correlations between a) the two or more second indicators for the other entity and b) the first recommendation and the second recommendation, a recommendation of an action to reduce risk for the other entity.

19. A system comprising one or more computers and one or more storage devices on which are stored instructions that are operable, when executed by the one or more computers, to cause the one or more computers to perform operations comprising:

receiving a request comprising two or more indicators of a first entity, the two or more indicators comprising a first indicator and a second indicator;

maintaining, in memory and for the first indicator, a first tree structure that identifies the first indicator and one or more first attributes that affect the first indicator, the first tree structure having i) one or more first parent nodes each of which represent indicators that are not actionable for the first entity and ii) one or more first leaf nodes each of which represent an action that can be performed for the first entity to adjust a value of the first indicator;

maintaining, in the memory and for the second indicator, a second tree structure that identifies the second indicator and one or more second attributes that affect the second indicator, the second tree structure having i) one or more second parent nodes each of which represent indicators that are not actionable for the first entity and ii) one or more second leaf nodes each of which represent an action that can be performed for the first entity to adjust a value of the second indicator;

determining, for the first indicator and using data that indicates actions performed for the first entity, whether the first tree structure for the first indicator includes a link with the second tree structure;

in response to determining that the first tree structure does not include the link with the second tree structure:

determining a weight for a link between the first tree structure and the second tree structure; and creating the link between the first tree structure and the second tree structure that includes the weight; and maintaining, in the memory, the first tree structure, the second tree structure, and the link between the first tree structure and the second tree structure that includes the weight for use in generating, using the second tree structure and the link that includes the weight, a recommendation of an action to adjust a value of the first indicator for an entity.

20. A non-transitory computer storage medium encoded with instructions that, when executed by one or more computers, cause the one or more computers to perform operations comprising:

receiving a request comprising two or more indicators of a first entity, the two or more indicators comprising a first indicator and a second indicator;

maintaining, in memory and for the first indicator, a first tree structure that identifies the first indicator and one or more first attributes that affect the first indicator, the first tree structure having i) one or more first parent nodes each of which represent indicators that are not actionable for the first entity and ii) one or more first leaf nodes each of which represent an action that can be performed for the first entity to adjust a value of the first indicator;

maintaining, in the memory and for the second indicator, a second tree structure that identifies the second indicator and one or more second attributes that affect the second indicator, the second tree structure having i) one or more second parent nodes each of which represent indicators that are not actionable for the first entity and ii) one or more second leaf nodes each of which represent an action that can be performed for the first entity to adjust a value of the second indicator;

determining, for the first indicator and using data that indicates actions performed for the first entity, whether the first tree structure for the first indicator includes a link with the second tree structure;

in response to determining that the first tree structure does not include the link with the second tree structure:

determining a weight for a link between the first tree structure and the second tree structure; and creating the link between the first tree structure and the second tree structure that includes the weight; and maintaining, in the memory, the first tree structure, the second tree structure, and the link between the first tree structure and the second tree structure that includes the weight for use in generating, using the second tree structure and the link that includes the weight, a recommendation of an action to adjust a value of the first indicator for an entity.

* * * * *